United States Patent
Kahlert et al.

(10) Patent No.: US 7,320,889 B2
(45) Date of Patent: Jan. 22, 2008

(54) CELL CULTIVATION DEVICE AND METHOD

(75) Inventors: Wolfgang Kahlert, Körle (DE); Bernd-Ulrich Wilhelm, Petershagen (DE); Rainer Salzmann, Melsungen (DE); Wolfgang Rietschel, Söhrewald (DE)

(73) Assignee: Sartorius Stedim Biotech GmbH, Goettingen (DE)

( * ) Notice: Subject to any disclaimer, the term of this patent is extended or adjusted under 35 U.S.C. 154(b) by 389 days.

(21) Appl. No.: 10/841,029

(22) Filed: May 7, 2004

(65) Prior Publication Data

US 2004/0229348 A1    Nov. 18, 2004

(30) Foreign Application Priority Data

May 15, 2003    (DE) ................. 103 22 054

(51) Int. Cl.
  *C12M 1/08*    (2006.01)
(52) U.S. Cl. ................. 435/295.3; 435/286.5; 435/286.6; 435/297.2; 435/299.1
(58) Field of Classification Search ............. 435/299.1, 435/299.2, 286.6, 293.1, 295.3, 297.2
See application file for complete search history.

(56) References Cited

U.S. PATENT DOCUMENTS

| | | | |
|---|---|---|---|
| 5,316,905 A * | 5/1994 | Mori et al. .................... | 435/3 |
| 5,501,971 A | 3/1996 | Freedman et al. | |
| 6,323,022 B1 * | 11/2001 | Chang et al. ............. | 435/286.5 |
| 7,033,823 B2 * | 4/2006 | Chang ..................... | 435/297.2 |
| 2003/0143727 A1 | 7/2003 | Chang | |

* cited by examiner

Primary Examiner—William H. Beisner
(74) Attorney, Agent, or Firm—Chernoff, Vilhauer, McClung & Stenzel, LLP

(57) ABSTRACT

A device and a method for the cultivation of cells is disclosed that utilizes external pneumatic pressure responsive to liquid level sensors to gently recirculate and cause turbulence in cell growth medium to promote cell growth without any shearing action and without a stir motor or mechanical manipulation means.

12 Claims, 3 Drawing Sheets

CELL CULTIVATION DEVICE AND METHOD

Pursuant to 35 USC §119, the priority of DE 103 22 054.2 filed May 15, 2003 is claimed.

BACKGROUND OF THE INVENTION

CESCO Bioengineering Co., Ltd. manufactures and sells its BelloCell® and BelloStage® Cell Culture System, comprising a device and method for cell cultivation. The device consists of a hollow cylinder in which a porous, fibrous matrix is located between an upper and a lower basket, the matrix serving as a bedding for the cells. An upper chamber is situated above, and a lower chamber below the bedding matrix. The lower chamber essentially consists of a compressible bellows-type bag, by means of which liquid cell growth medium can be recirculated to the upper chamber. One drawback of this device is that during the expansion of the bellows-type bag, a vacuum is generated, which causes a cell-shearing action, which of course is detrimental to the cultivation of cells. Another drawback is that relatively complex mechanical apparatus is needed to control the expansion and contraction of the bellows-type bag. A third drawback of this device is that it requires operation only under clean-room conditions, adding substantial expense.

U.S. Pat. No. 5,501,971 discloses a method and apparatus for cultivating cells in a reactor that includes a basket-type packed bed and an internal liquid cell growth medium recirculation device consisting of a stirrer. The principal drawback of this reactor is that the stirrer requires mechanical maintenance and must be supplied with electrical power for the reactor to operate properly.

There is therefore needed in the art a cell cultivation reactor that avoids any cell-shearing action and dispenses with the need for a mechanical drive and that can be operated under non-clean-room conditions.

These needs are met by the present invention, which is summarized and described in detail below.

BRIEF SUMMARY OF THE INVENTION

In a first aspect, the invention comprises a cell cultivation reactor consisting of a cylinder with an upper cap, the cylinder being placed in a reactor vessel with a sealable lid, whereby a surrounding cell culture chamber is formed; the cell culture chamber is provided with liquid level sensors. The cylinder is situated between a liquid-permeable upper plate and a liquid-permeable lower plate, and is filled with a bedding matrix. The cylinder also has an antechamber between the upper plate and the upper cap. Optionally the cell culture chamber may be provided with a gasification tube. The level of liquid cell growth medium in the cell culture chamber is maintained and circulated through the bedding matrix by the relay of information from the liquid level sensors. Because the reactor is sealed and the fluid level is maintained and circulated strictly by pneumatic pressure, cell-shearing is prevented, there is no need for clean-room conditions and mechanical stirrers and other mechanical circulation means are dispensed with.

Figure 1:
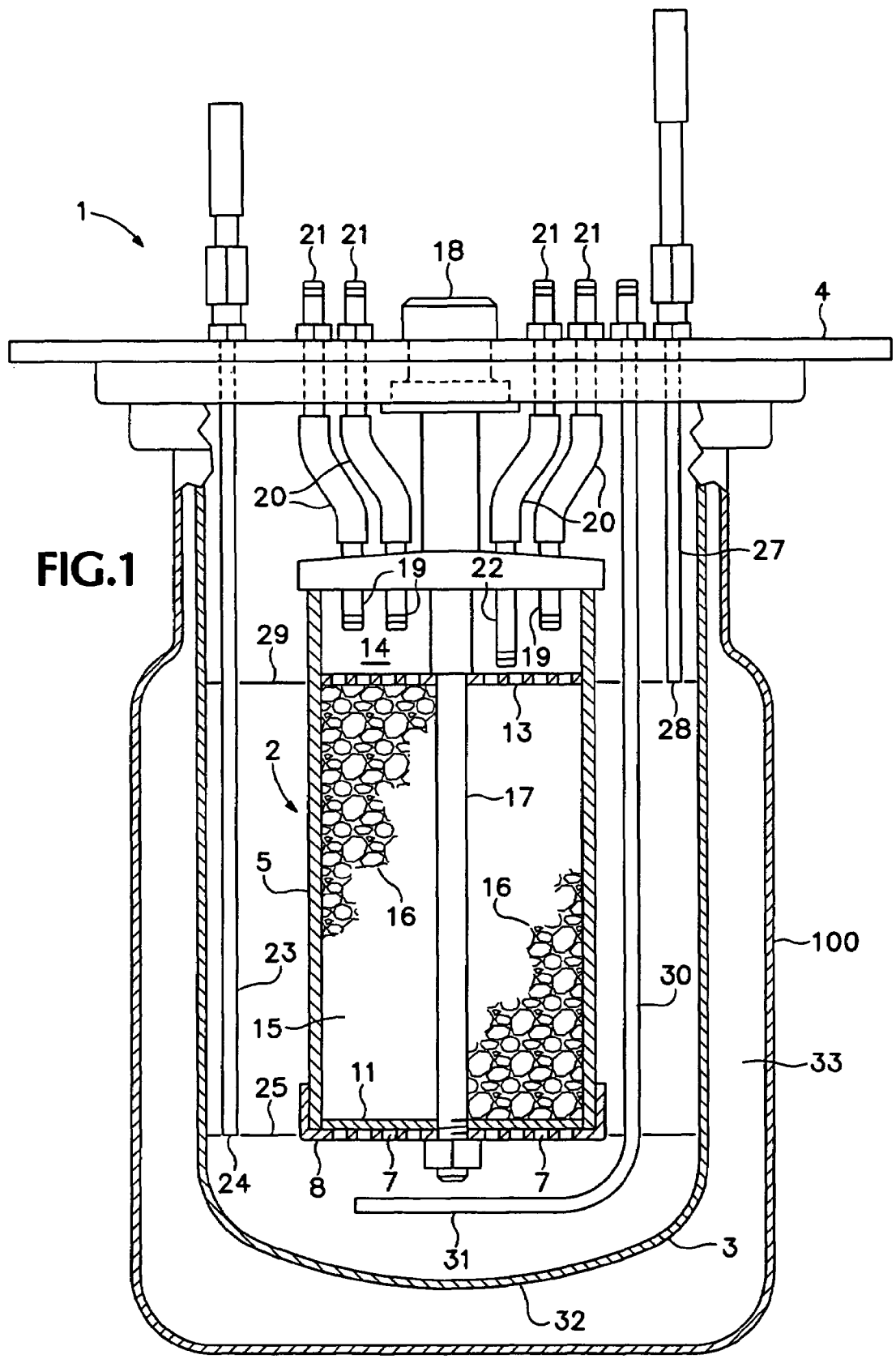
FIG. 1 is a side view of an exemplary cell cultivation reactor of the invention.

In a second aspect the invention comprises a method for the cultivation of cells in the above reactor wherein liquid cell growth medium is circulated from the antechamber through the bedding matrix and into the cell culture chamber without any mechanical means.

DETAILED DESCRIPTION OF PREFERRED EMBODIMENTS

In accordance with the invention, a cylinder is placed within a reactor vessel with a lid to form a cell culture chamber surrounding the cylinder. The culture chamber is provided with an upper liquid level sensor and a lower liquid level sensor, and the level of liquid cell growth medium in the culture chamber is pneumatically controlled by external sensing and control means connected in operative relationship with the liquid level sensors. The liquid cell growth medium is circulated through pores in upper and lower plates situated between the antechamber and the cell culture chamber. Where pores in the upper and lower plates are concerned, these may be, for example, pores in membranes or mesh openings in sieves.

By placement of the cylinder in a sealable cell culture chamber, the reactor may be operated without any need for establishing clean-room conditions. A change of liquid cell growth medium can be effected through fittings and hoses which can be sterilized. By adjusting and manipulating the fluid level in the reactor, the use of mechanical drives and the generation of a vacuum and cell-shearing action can be completely avoided.

In a preferred embodiment of the invention, the direction of flow and rate of circulation of the liquid cell growth medium is pneumatically controlled by one or more pressure valves. The arrangement of this embodiment allows the predetermination of the circulation rate of liquid cell growth medium by preset adjustments of pressure and time the pressure is applied. In this manner a gentle turbulence of the liquid cell growth medium may be effected, which facilitates and enhances the growth of the cells immersed in the cell growth medium. The degree of turbulence can be adjusted to meet the growth requirements of various types of cells.

In a preferred embodiment of the invention, the upper and lower plates are sieves, which are easily adapted to the requirements of continuous cell cultivation. As an example, for Chinese Hampster Ovary (CHO) cells, the lower sieve may have pores or mesh openings of about 10 μm in diameter, while the upper sieve may have a somewhat larger porosity or mesh opening.

In another preferred embodiment of the invention, the upper and lower plates comprise microporous membranes, through which growth-restricting byproducts and cell fragments can freely pass. To meet this requirement, the lower membrane should have porosity such that cells and bedding matrix material may not pass through the membrane. Thus, the membranes should be chosen so that, as needed, high molecular weight proteins, such as antibodies and the like can be allowed to either selectively pass through the membrane or to be blocked by the membrane.

The upper membrane may be the same as the lower membrane or it may be fabricated so that cell fragments are transported or floated up to the antechamber where they are allowed to accumulate. In order to assure the mechanical stability of the membranes, they can be reinforced by a support grid. Suitable bedding matrix material includes porous ceramic material, polymeric fibrous material or other material of a ceramic origin.

In yet another advantageous embodiment of the invention, the liquid cell growth medium is either forced into or out of the cylinder by means of a pressurized gas or gas mixture. A gas or gas mixture is preferably used which is optimal for cell growth. The pH of the growth medium and/or its oxygen content (measured by the partial pressure of oxygen or $pO_2$) can also be adjusted by the introduction of gas or a gas mixture. It is possible to directly introduce gas into the liquid cell growth medium by a gasification tube placed into the cell culture container.

Referring to the drawings, wherein the same numerals refer to the same elements, there is shown a cell cultivation reactor 1 essentially comprising a cylinder 2 situated in a cell culture chamber 3 surrounding cylinder 2, cell culture chamber in turn being within a reactor vessel 100 that is capped with a reactor vessel lid 4; cell cultivation takes place within the space 33 surrounding cylinder 2. Cylinder 2 consists of an outer shell 5 which has on its lower end 6 a base plate 8, the base plate being provided with multiple fluid flow-through openings 7. Outer shell 5 is capped by an upper cap 10. Cylinder 2 has a lower plate 11 situated close to base plate 8, lower plate 11 being in the form of a liquid-permeable sieve or porous membrane. Upper plate 13 is located at a distance 12 above lower plate 11, forming an antechamber 14 between upper plate 13 and upper cap 10. A bedding containment chamber 15 is defined by outer shell 5 and lower and upper plates 11 and 13, respectively. Cell bedding matrix material 16 is contained by bedding containment chamber 15; the matrix material promotes cell cultivation. Upper cap 10 and base plate 8 may be held together by an axially oriented tension rod 17.

Upper cap 10 has a fastening attachment 18 centered therein, by which it can be secured to reactor vessel lid 4; preferably fastening attachment 18 is of a threaded nut-and-bolt configuration, wherein corresponding female threads are found in reactor vessel lid 4. Upper cap 10 is also provided with pneumatic connection fittings 19, which, by means of silicone hoses 20, can be placed in fluid communication with pneumatic fittings 21 of reactor vessel lid 4, thereby creating fluid communication between the interior and exterior of the reactor vessel. A longer pneumatic connection fitting 22 in upper cap 10 preferably terminates immediately above upper plate 13, while the other connection fittings 19 preferably terminate at a somewhat greater distance above upper plate 13.

A lower liquid level sensor 23 is attached to and through reactor vessel lid 4, and its tip 24 terminates at a predetermined minimum lower level 25 of the liquid cell growth medium in culture chamber 3. Upper liquid level sensor 27 is also secured to and through reactor vessel lid 4 so that its tip 28 is at a predetermined maximum level of the liquid cell growth medium in the culture chamber. A gasification tube 30 may also be secured to and through reactor vessel lid 4, the lower end 31 of which is proximal to the bottom 32 of culture chamber 3. Liquid level sensors 23 and 27, and, if necessary, further sensors (not shown) may be connected to external apparatus (not shown) for measurement and control of pH, oxygen content, fluid level and degree of turbulence of the liquid cell growth medium.

EXAMPLE

Figure 2:
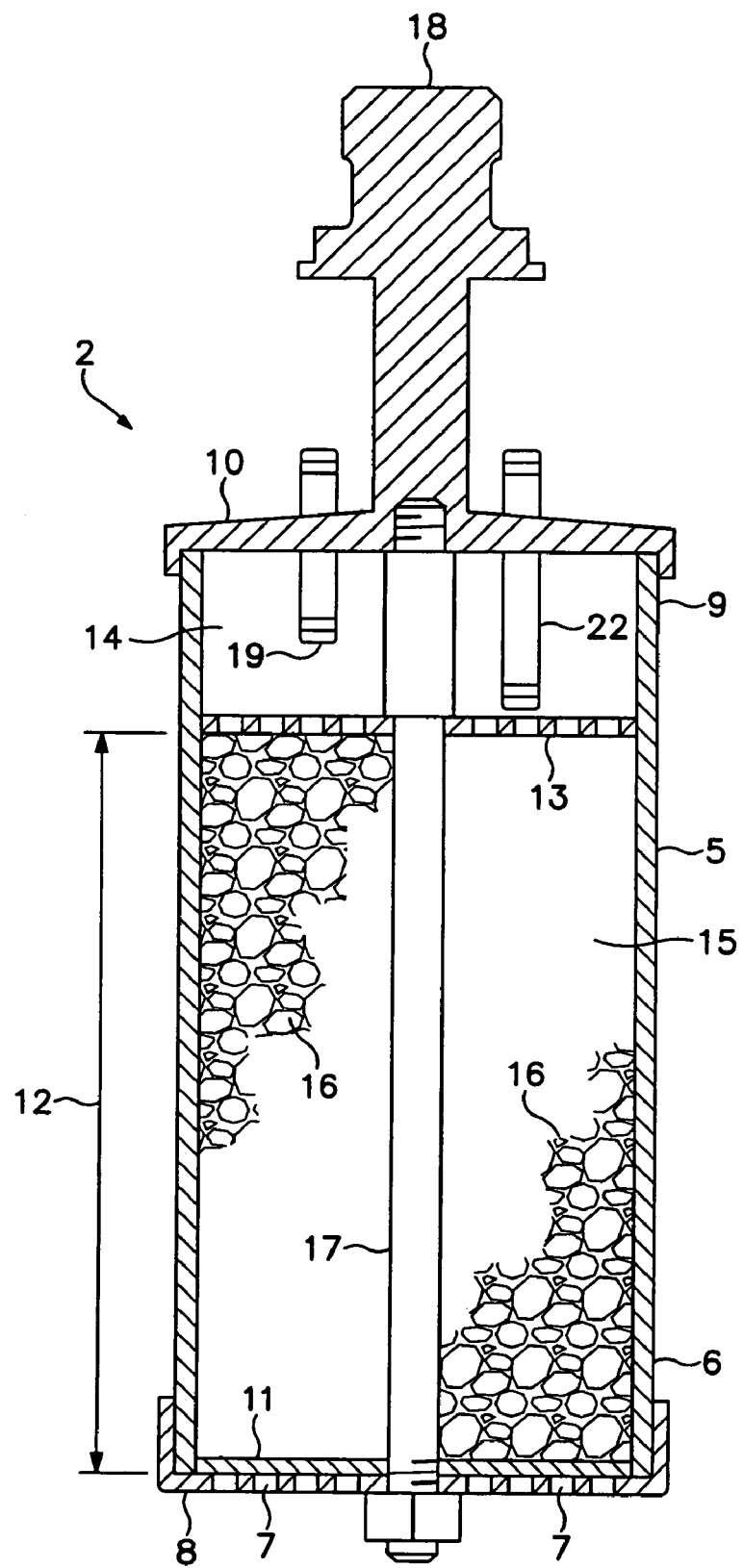
FIG. 2 is a cross-sectional view of the cylinder portion of the reactor shown in FIG. 1 without cell growth bedding matrix.
Figure 3:
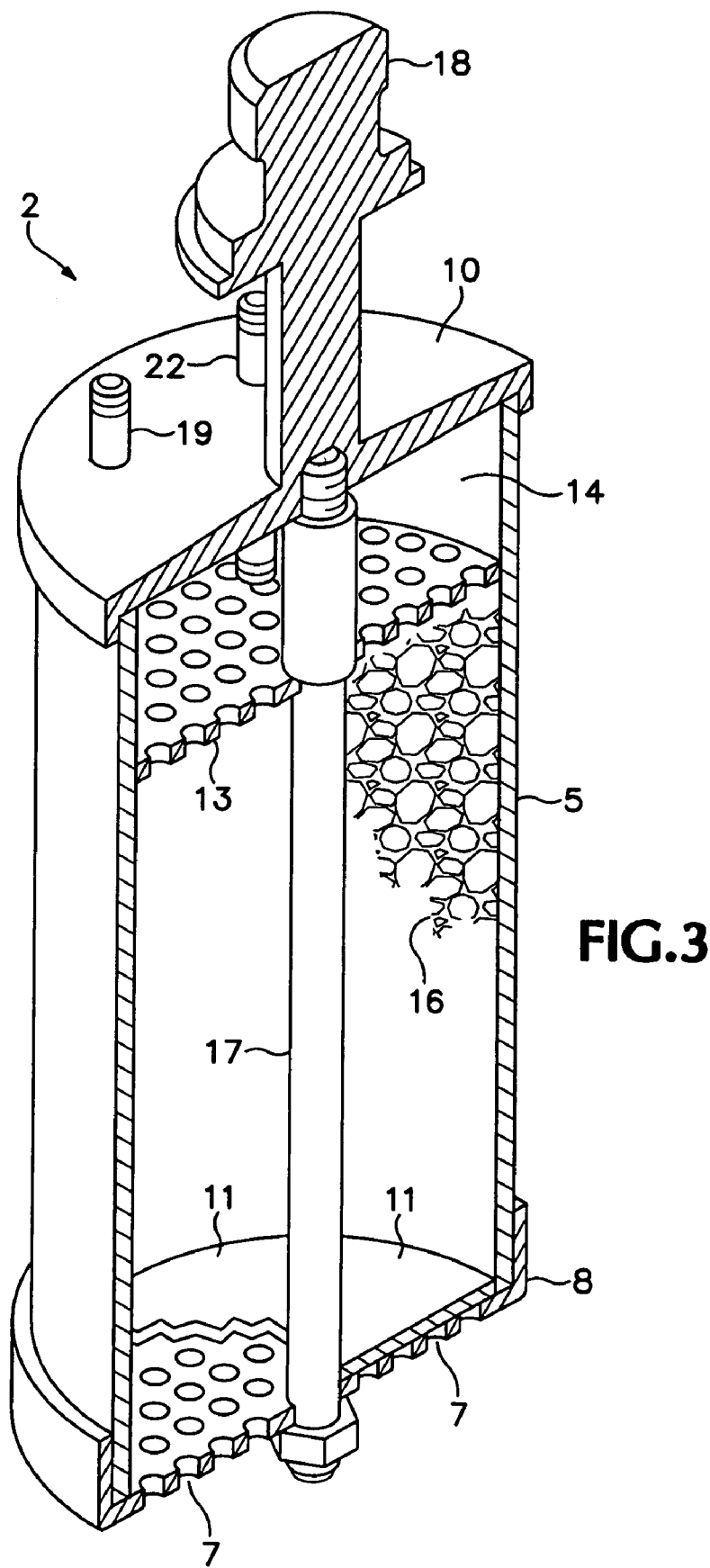
FIG. 3 is a cutaway sectional view of the cylinder shown in FIG. 2, but containing cell growth bedding matrix.

A cell growth reactor of substantially the same configuration shown in FIGS. 1-3 is assembled. Cylinder 2 is provided with lower and upper plates 11 and 13, respectively; when CHO cells are to be cultivated, a sieve having mesh openings 10 µm in diameter can be employed as lower plate 11, which coacts with upper plate 13, the upper plate having a larger mesh sieve.

Cylinder 2 is filled with bedding matrix material 16 such as Sponceran® from Zellwerk AG, a porous ceramic substance. Reactor vessel lid 4 is secured to the reactor vessel to form a fluid-tight seal. In this arrangement, pneumatic fittings 19 and 22 of upper cap 10 are connected via silicone hoses 20 to pneumatic fittings 21 on reactor vessel lid 4. Longer fitting 22 and one of the shorter fittings 19 are connected by a silicon hose employing couplings (not shown) which, following sterilization, provide sterile connection of the hoses. Bound onto two other connection fittings 19 is a sterile membrane filter (not shown). Liquid level sensors 23 and 27 are respectively adjusted to the desired lower liquid level 25 and upper liquid level 29, which are the minimum and maximum liquid levels, representing the minimum and maximum volumes of liquid cell growth medium in culture chamber 3.

To operate the cell cultivation device, cell culture chamber 3 is first filled with about 300 to 500 mL of pure water and then sterilized, preferably in an autoclave. The water is then removed from culture chamber 3 and refilled with sterile liquid cell growth medium. The composition of the cell growth medium depends upon the cell lineage and/or on the desired product. Culture chamber 3 is next connected to external measurement and control apparatus and all of the steps necessary for cell cultivation are carried out, including calibration of liquid level sensors, adjustment of control software, etc. An inoculation vial (not shown) containing cells to be cultivated is placed in fluid communication with the interior of bedding containment chamber 15 via fitting 21 so as to grow, e.g., CHO cells of a lineage which produces proteins. By a very small displacement of the upper and lower levels of the liquid cell growth medium, which also determines the rate of circulation of the cell growth medium, the growth of the cells on the bedding matrix material 16 is promoted. Cell growth can be monitored by the periodic withdrawal of a sample from longer connection fitting 22, which will show whether the frequency of liquid growth medium displacement and/or its rate of circulation is meeting the growth requirements of the cells.

Gasification, pH and $pO_2$ may be adjusted by introducing an appropriate gas/gas mixture, the pressure of which also forces liquid cell growth medium out of cylinder 2 and into culture chamber 3. The cell growth medium can be gasified directly through gasification tube 30. Necessary adjustment of the composition of the cell growth medium, such as removal of growth-inhibiting substances, replenishing nutrients and the frequency of such adjustments is carried out in culture chamber 3. Such adjustment depends, for example, on both the composition of the cell growth medium and the "health" of the cells. Living cells are retained by the 10 µm sieve in cylinder 2. With the use of a 10 µm sieve the target product such as proteins is found in the exchanged cell growth fluid medium 26 in culture chamber 3. Product recovery, concentration and purification is then conducted in accordance with conventional practices in cell cultivation.

With the use of a membrane instead of a 10 µm sieve, cell waste product is transported into cell growth medium 26 of culture chamber 3, and the target protein/products are retained not in culture chamber 3, but instead in cylinder 2. In this case, the target product may be recovered by filling cylinder 2 all the way up to upper cap 10. Subsequently, the resulting supernatant layer containing the target product is decanted or drained off, whereupon the product is recovered, concentrated and purified according to conventional practices.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

The invention claimed is:

1. A cell cultivation device comprising:
   (a) a reactor vessel with a lid;
   (b) a matrix-containing chamber within said reactor vessel, said matrix-containing chamber comprising a cylinder having a base and an upper cap separate from said lid, a liquid-permeable upper plate and a liquid-permeable lower plate both within said cylinder, a liquid-permeable matrix between said upper plate and said lower plate, whereby an antechamber is formed by said upper plate, the wall of said cylinder and said upper cap;
   (c) a cell culture chamber within said reactor vessel and surrounding said cylinder;
   (d) an upper liquid level sensor and a lower liquid level sensor within said cell culture chamber; and
   (e) at least two hydraulic fittings through said upper cap and extending into said antechamber so as to place said antechamber in fluid communication with the exterior of said upper cap.

2. The device of claim 1 wherein said upper plate and said lower plate each comprise a sieve.

3. The device of claim 1 wherein said upper plate and said lower plate each comprise a porous membrane.

4. The device of claim 3 wherein said membrane has a membrane support.

5. The device of any of claims 1-4 wherein said matrix is selected from the group consisting of a ceramic material, a fibrous material and a polymeric material.

6. The device of any of claims 1-4 wherein said cell culture chamber has a gasification tube through which gas may pass.

7. The device of any of claims 1-4 including liquid cell growth medium within said cell culture chamber.

8. The device of claim 7 wherein the upper and lower levels of said liquid cell growth medium are sensed by said upper liquid level sensor and said lower liquid level sensor, respectively.

9. The device of claim 8 wherein the level of said liquid cell growth medium is maintained at predetermined upper level by the relay of information from said upper liquid level sensor and said lower liquid level sensor.

10. The device of claim 9 wherein said liquid cell growth medium is circulated through said matrix by the application of pneumatic pressure through said at least two hydraulic fittings.

11. The device of claim 7 further comprising means for adjusting the pH of said liquid cell growth medium by the introduction of at least one gas.

12. The device of claim 7 further comprising means for adjusting the oxygen content of said liquid cell growth medium by the introduction of at least one gas.

* * * * *